(12) United States Patent
Yamamoto et al.

(10) Patent No.: US 6,437,164 B1
(45) Date of Patent: Aug. 20, 2002

(54) PROCESS FOR THE PREPARATION OF PHOSPHONITE COMPOUNDS

(75) Inventors: Masataka Yamamoto; Masahiro Kasagi, both of Fukuoka; Takashi Yokomatsu, Mie; Akio Mishima, Fukuoka; Yoshihiro Ozaki, Osaka, all of (JP)

(73) Assignee: Yoshitomi Fine Chemicals, Ltd., Osaka (JP)

( * ) Notice: Subject to any disclaimer, the term of this patent is extended or adjusted under 35 U.S.C. 154(b) by 0 days.

(21) Appl. No.: 09/869,865

(22) PCT Filed: Jan. 6, 2000

(86) PCT No.: PCT/JP00/00029

§ 371 (c)(1),
(2), (4) Date: Jul. 6, 2001

(87) PCT Pub. No.: WO00/40587

PCT Pub. Date: Jul. 13, 2000

(30) Foreign Application Priority Data

Jan. 6, 1999 (JP) .............................................. 11-1505

(51) Int. Cl.$^7$ ................................................. C07F 9/48
(52) U.S. Cl. ........................... 558/71; 558/70; 558/156; 558/96
(58) Field of Search .............................. 558/96, 70, 71, 558/156

(56) References Cited

U.S. PATENT DOCUMENTS

| | | | |
|---|---|---|---|
| 5,300,257 A | * 4/1994 | Akashi et al. | 252/400.24 |
| 5,703,150 A | * 12/1997 | Ike et al. | 524/125 |
| 5,840,954 A | * 11/1998 | Quotschalla et al. | 558/71 |
| 6,362,358 B1 | * 3/2002 | Gronmaier et al. | 558/95 |

FOREIGN PATENT DOCUMENTS

| | | |
|---|---|---|
| EP | 516006 | * 12/1992 |
| JP | 08-253491 | * 10/1996 |
| JP | 10-338777 | * 12/1998 |

* cited by examiner

*Primary Examiner*—Fiona T. Powers
(74) *Attorney, Agent, or Firm*—Wenderoth, Lind & Ponack, L.L.P.

(57) ABSTRACT

Biphenyl and phosphorus trichloride are reacted in the presence of aluminum chloride, a hydrogen chloride gas generated is removed, a pyridine is added, excess phosphorus trichloride is removed, a resulting reaction product containing the obtained phosphine compound of the formula:

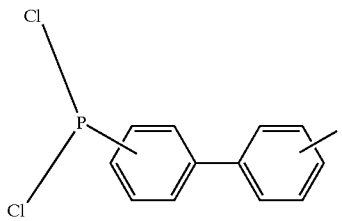

and a phenol compound of the formula:

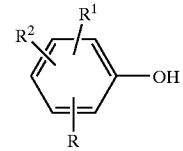

wherein R is a hydrogen atom or methyl and $R^1$ and $R^2$ are each a hydrogen atom or alkyl having 1 to 5 carbon atoms, are reacted in the presence of a base as a deacidifying agent, and hydrochloride of this base and a pyridine-aluminum chloride complex are removed. By this method, a high quality phosphonite compound containing phosphinobiphenylene of the formula:

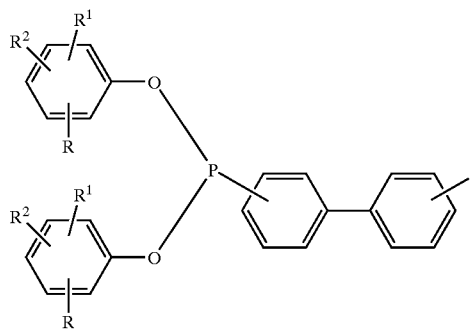

can be produced safely in a high yield.

25 Claims, No Drawings

PROCESS FOR THE PREPARATION OF PHOSPHONITE COMPOUNDS

This application is a 371 of PCT/JP00/00029 filed Jan. 6, 2000.

TECHNICAL FIELD

With the effects of preventing oxidation and coloring of organic polymer materials during forming processes, improving weatherability and the like, biphenylenediphosphonite compounds contribute to the addition of high value to organic polymer materials, and their usefulness has been considered to be significant. The present invention relates to a method for producing a phosphonite compound containing phosphinobiphenylene of the formula (I'):

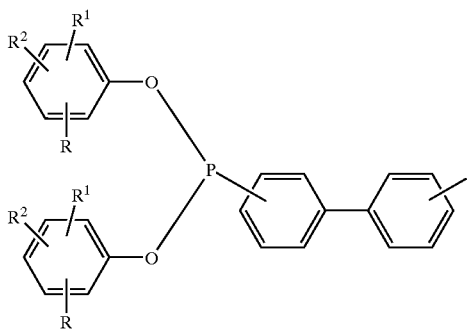

wherein R is a hydrogen atom or methyl and $R^1$ and $R^2$ are each a hydrogen atom or alkyl having 1 to 5 carbon atoms [hereinafter to be also referred to as phosphinobiphenylene of the formula (I')], which is useful as a stabilizer of organic polymer materials, and to a method for preventing thermal decomposition of the phosphonite compound when heating a solution containing the phosphonite compound.

BACKGROUND ART

There are conventionally known methods for producing a phosphonite compound containing phosphinobiphenylene of the formula (I'), such as (A) a method including forming a complex with aluminum chloride from a reaction product of aluminum chloride, biphenyl and phosphorus trichloride, by the use of phosphorus oxychloride as a complex forming agent, subjecting this complex to filtration and removal, thereby to isolate halogenated phosphine, and subsequently reacting this compound with a phenol compound, such as 2,4-di-tert-butylphenol and the like, in the presence of triethylamine (JP-B-50-35096), (B) a method including removing excess phosphorus trichloride from a reaction product of aluminum chloride, biphenyl and phosphorus trichloride and adding dropwise the obtained halogenated phosphine-aluminum chloride complex to a mixture of pyridine and the aforementioned phenol compound to allow reaction (JP-A-2-270892), (C) a method including reaction of phosphorous acid-bis(2,4-di-tert-butylphenyl)ester-chloride with a Grignard compound obtained from 4,4'-dihalobiphenyl and magnesium (JP-A-2-221290) and (D) a method including adding ethers, such as diethyl ether and the like, as a complex forming agent to a reaction product of biphenyl and phosphorus trichloride in the presence of aluminum chloride, and reacting the obtained mixture with 2,4-di-tert-butyl-5-methylphenol and the like in the presence of a deacidifying agent (JP-A-8-253491) and the like.

In the production method of the aforementioned (A), it is necessary to use phosphorus oxychloride as a complex forming agent to isolate halogenated phosphine, and to filtrate and separate the generated phosphorus oxychloride-aluminum chloride complex. However, this complex has hygroscopicity, and in addition, shows filtration property that is not necessarily fine. Combined with the difficulty in recovering phosphorus oxychloride from this complex and problems both in the aspects of method and cost, this method is not an industrially beneficial production method. Moreover, since halogenated phosphine is designated as a mutagenic compound in Industrial Safety and Health Law, the operation for isolation is problematic in view of the safety to human body.

According to the production method of the aforementioned (B), phosphorus trichloride is distilled away, without forming a complex, in the presence of aluminum chloride, which leads to a defect in that polyphosphine chloride is generated as the reaction proceeds. As a result, the composition of the objective phosphonite compound varies depending on the conditions of distillation. The reaction concentrate becomes a glass-like compound having a very high viscosity at normal temperature, which can afford sufficient flowability for dropwise addition only upon heating. According to this method, moreover, heat generation during forming of a complex of pyridine and aluminum chloride in the first phase and that during deacidifying reaction by pyridine in the second phase occur at the same time. For a large-scale production, therefore, facility such as a large-sized cooling system and the like is required, which makes this method unbeneficial for industrial production in view of the operability and facility cost. Furthermore, filtration at a low temperature of $-10°$ C. to remove a complex of pyridine and aluminum chloride remaining in the reaction product after separation of the complex is disclosed. The complex of pyridine and aluminum chloride is a hygroscopic and viscous substance, which is extremely difficult to apply to industrial filtration. As described in JP-A-5-230282, insufficient removal of aluminum chloride leads to easy hydrolysis of the objective compound, which is a fatal defect.

According to the production method of the aforementioned (C), the use of 4,4'-dihalobiphenyl containing polychloride biphenyl (PCB) as a starting material poses a serious problem. Moreover, production of Grignard compound requires a large amount of tetrahydrofuran solvent, while requiring separate and selective production of phosphorous acid-bis(2,4-di-tert-butylphenyl)ester-chloride under the conditions free of generation of phosphorous acid-tris(2,4-di-tert-butylphenyl)ester. In view of such defects, this method is not satisfactory.

According to the production method of the aforementioned (D), separation for recovery of ether as a complex forming agent and a deacidifying agent requires a lot of time and labor. Thus, this method is not industrially beneficial.

The products obtained by any of the aforementioned production methods (A)–(D) contain comparatively large amounts of unreacted phenol compounds, such as 2,4-di-tert-butyl-5-methylphenol, 2,4-di-tert-butylphenol compound and the like, which causes time-course coloring, degradation of properties (lower stabilizing action) and the like of the product. Ultimate removal of unreacted phenol compound by distillation may be one solution, but removal of unreacted phenol compound by distillation requires heating to $150°$ C. or above under reduced pressure, which in turn causes partial decomposition of the objective phosphonite compound during distillation. Therefore, there is a demand on a method for obtaining the objective product free of unreacted phenol compounds as impurities, which does not cause thermal decomposition of the objective phosphonite compound.

The present invention has been made in view of the above-mentioned situation, and aims at providing a method by which a high quality phosphonite compound containing phosphinobiphenylene of the aforementioned formula (I') can be produced safely and in high yields, as well as a method for preventing thermal decomposition of the phosphonite compound when heating a solution containing the phosphonite compound.

DISCLOSURE OF THE INVENTION

The present inventors have conducted intensive studies in an attempt to solve the above-mentioned problems and arrived at the following findings (i)–(iv).

(i) When biphenyl and excess phosphorus trichloride are reacted in the presence of aluminum chloride and pyridines are added to the resulting reaction product to form a pyridine-aluminum chloride complex, after which the mixture is heated (for example, heating to 60–100° C.) to distill away the excess phosphorus trichloride, phosphorus trichloride can be distilled away efficiently and the residual amount of phosphorus trichloride can be made extremely small, because the viscosity of the reaction product can be lowered (improved flowability of reaction product) due to the addition of pyridines and heating. Moreover, since aluminum chloride is deactivated by the formation of the complex, the production of polyphosphine chloride, which occurs as the reaction proceeds, can be suppressed when phosphorus trichloride is distilled away.

(ii) When, for example, a phenol compound, such as 2,4-di-tert-butylphenol, 2,4-di-tert-butyl-5-methylphenol, 2,4-di-tert-butyl-6-methylphenol and the like, is added to the reaction product, from which the above-mentioned phosphorus trichloride has been distilled away, and then a base comprising amine such as pyridine and the like is added dropwise as a deacidifying agent to synthesize the objective phosphonite compound containing phosphinobiphenylene of the formula (I'), the reaction for forming the aforementioned pyridine-aluminum chloride complex (exothermic reaction) and the reaction for producing the objective phosphonite compound containing phosphinobiphenylene of the formula (I') (exothermic reaction caused by dropwise addition of base as a deacidifying agent) can be separated, and heat generation can be controlled extremely easily. A phosphonite compound containing phosphinobiphenylene of the formula (I') can be synthesized without the need to remove biphenyl chlorophosphine, which is highly stimulating to human body, from the reaction product, thereby securing the safety of the workers.

(iii) A pyridine-aluminum chloride complex and hydrochloride of the base can be separated and removed by partitioning from the reaction product after synthesis of the phosphonite compound containing phosphinobiphenylene of the formula (I') of the above-mentioned (ii). By treating a solution containing phosphonite compound, from which a pyridine-aluminum chloride complex and hydrochloride of base have been removed, with, for example, alkali or a salt thereof, such as alkali metal hydroxide and the like, the pyridine-aluminum chloride complex can be removed, thereby preventing the hydrolysis of the phosphonite compound (glass-like solid) obtained by removing the solvent thereafter.

(iv) By the addition of hindered amine to a solution containing phosphonite compound after synthesis, heat stability of the phosphonite compound can be improved, thus enabling sufficient concentration by heating the solution. As a result, not only the solvent but the residual phenol compound can be efficiently removed.

The present invention has been completed based on the findings of the above-mentioned (i)–(iv) and is characterized by the following.

(1) A method for producing a phosphonite compound comprising phosphinobiphenylene of the formula (I'), which method comprising reacting biphenyl and phosphorus trichloride in the presence of aluminum chloride, removing a hydrogen chloride gas generated, adding a pyridine, removing excess phosphorus trichloride, reacting a resulting reaction product containing a phosphine compound of the formula (II'):

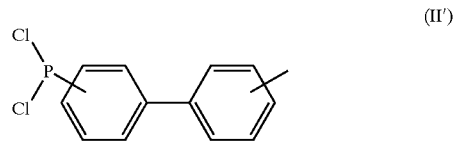

(II')

[hereinafter to be also referred to as phosphine compound (II')] and a phenol compound of the formula (III'):

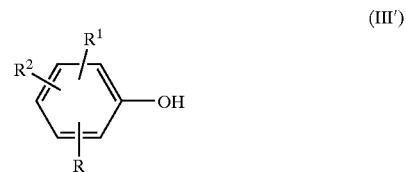

(III')

wherein R is a hydrogen atom or methyl and $R^1$ and $R^2$ are each a hydrogen atom or alkyl having 1 to 5 carbon atoms [hereinafter to be also referred to as phenol compound of the formula (III')] in the presence of a base as a deacidifying agent, and removing hydrochloride of said base and a pyridine-aluminum chloride complex [hereinafter the phosphonite compound is to be also referred to as phosphonite compound (I')].

(2) A method for producing a phosphonite compound comprising at least one phosphinobiphenylene of the formula (I):

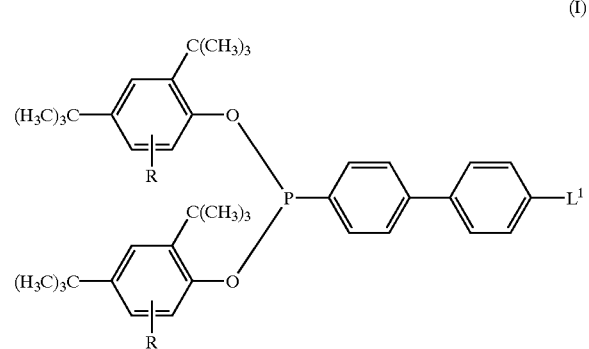

(I)

wherein R is a hydrogen atom or methyl and $L^1$ is a hydrogen atom, a group of the formula:

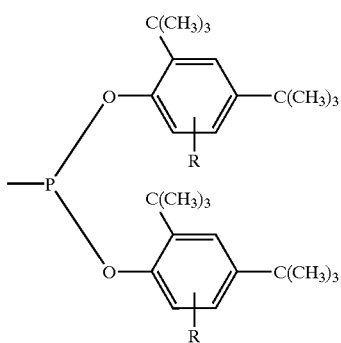

wherein R is as defined above, a group of the formula:

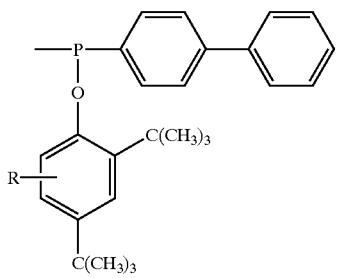

wherein R is as defined above, or a group of the formula:

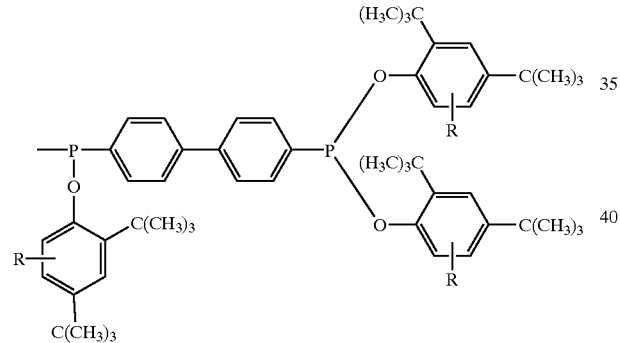

wherein R is as defined above, [hereinafter to be also referred to as phosphonite compound of the formula (I)], which method comprising reacting biphenyl and phosphorus trichloride in the presence of aluminum chloride, removing a hydrogen chloride gas generated, adding a pyridine, removing excess phosphorus trichloride, reacting a resulting reaction product containing at least one phosphine compound of the formula (II):

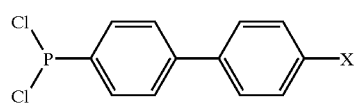
(II)

wherein X is a hydrogen atom, —PCl$_2$,

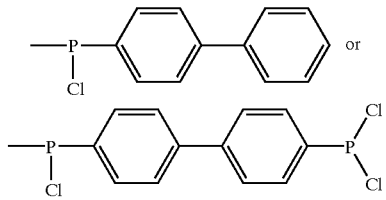
or

[hereinafter to be also referred to as phosphine compound of the formula (II)] and a phenol compound of the formula (III):

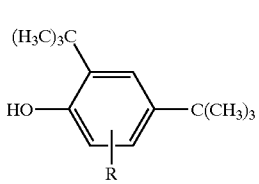
(III)

wherein R is a hydrogen atom or methyl [hereinafter to be also referred to as phenol compound of the formula (III)] in the presence of a base as a deacidifying agent, and removing hydrochloride of said base and a pyridine-aluminum chloride complex.

(3) The method for producing a phosphonite compound according to (2) above, wherein the phosphonite compound of the formula (I) comprises a compound of the formula (Ia):

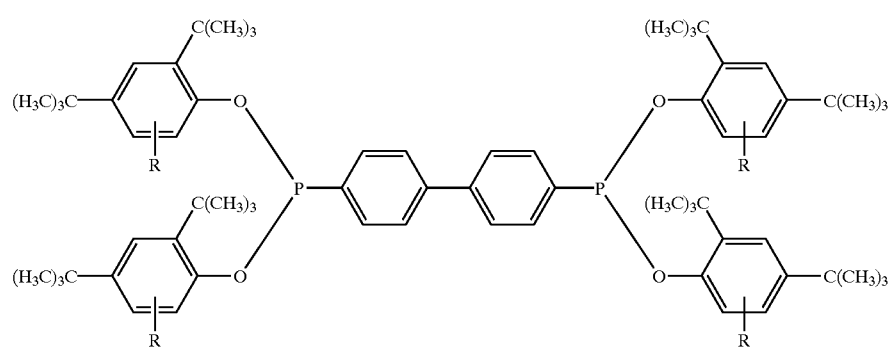
(Ia)

wherein R is a hydrogen atom or methyl [hereinafter to be also referred to as a compound of the formula (Ia)] and may further comprise at least one compound selected from compounds of the formula (Ib):

(Ib)

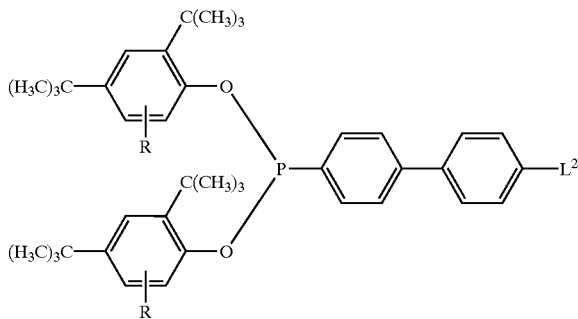

wherein R is a hydrogen atom or methyl and $L^2$ is a hydrogen atom, a group of the formula:

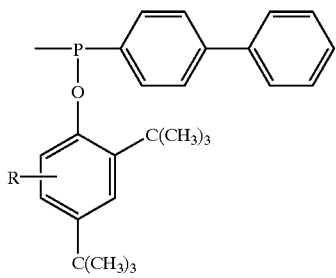

wherein R is as defined above, and a group of the formula:

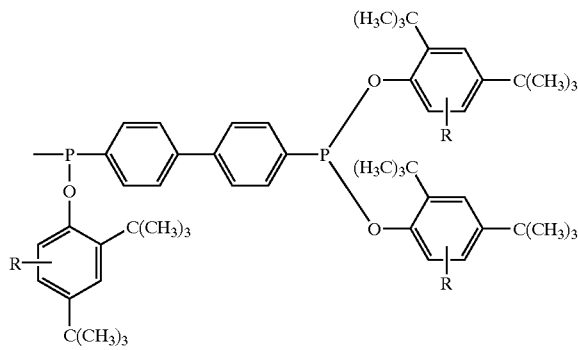

wherein R is as defined above, [hereinafter to be also referred to as a compound of the formula (Ib)].

(4) The method according to any of the above-mentioned (1) to (3), wherein the hydrochloride of base and the pyridine-aluminum chloride complex are removed and the obtained crude product is treated with alkali or a salt thereof.

(5) The method according to (4) above, wherein, after the treatment of the crude product with alkali or a salt thereof, an unreacted phenol compound is removed.

(6) The method according to any of the above-mentioned (1) to (3), wherein, after the treatment of the hydrochloride of base and the pyridine-aluminum chloride complex, the obtained crude product is treated with alkali or a salt thereof and then with hindered amine.

(7) The method according to (6) above, wherein, after the treatment of the crude product with hindered amine, an unreacted phenol compound is removed.

(8) A method for preventing thermal decomposition of a phosphonite compound, which method comprises heating a solution containing a phosphonite compound (I') or a solution containing a phosphonite compound of the formula (I) at not less than 150° C. in the presence of hindered amine.

According to the present invention, a phosphine compound (phosphine compound (II')) having a group of the aforementioned formula (II') is synthesized in a first phase.

Biphenyl and excess phosphorus trichloride are reacted in the presence of aluminum chloride for about 1–8 h. The phosphorus trichloride is used in a 3 to 8-fold molar amount, preferably 4 to 6-fold molar amount, per mole of biphenyl, and aluminum chloride is used in a 1.6 to 3.0-fold molar amount, preferably 1.8 to 2.6-fold molar amount, per mole of biphenyl. By changing the amount to be charged of aluminum chloride and the reaction time, the composition of the reaction product containing a phosphine compound generated can be adjusted. With respect to the phosphonite compound (phosphonite compound (I')) containing phosphinobiphenylene, which is the object of the present invention, a phosphonite compound of the formula (I) is superior in the effect as a stabilizer of organic polymer materials, and of the phosphonite compounds of the formula (I), a phosphonite compound of the formula (Ia) shows particularly superior stabilization effect. Therefore, the reaction is preferably carried out such that phosphine compound of the formula (II), particularly that wherein the substituent at X is —PCl$_2$, is generated in a greater amount. In such reaction, a hydrogen chloride gas is generated, but can be removed by, for example, adsorption to an aqueous alkali solution.

The pyridines are added to the above-mentioned reaction product after reaction as a complex forming agent to form a pyridine-aluminum chloride complex. Examples of the pyridines include π deficient aromatic N-heterocyclic compounds such as pyridine, picoline, lutidine, collidine, quinoline, isoquinoline, pyrazine, aminopyridine, pyridazine, pyrimidine, cinnoline, pteridine and the like. The pyridines are beneficially the same compound as the base to be used as a deacidifying agent in the next step (second phase) for the reaction of a reaction product containing the phosphine compound and a phenol compound of the formula (III') [e.g., the formula (III)] in view of workability and reusability.

The pyridines are used in a proportion of 0.8–1.5 equivalents, preferably 0.9–1.1 equivalents, relative to aluminum chloride. The complex is preferably formed in a temperature range of from 40° C. to the boiling point of phosphorus trichloride. After the complex forming, excess phosphorus trichloride is removed by evaporation at generally 50–100° C., preferably 60–90° C., at a normal pressure or under reduced pressure.

In this way, a reaction product containing a phosphine compound (II') can be obtained. The reaction product may contain a compound of the formula (Ia), and further at least one compound selected from the compounds of the formula (Ib).

In a second phase, to the thus-obtained reaction product containing a phosphine compound (II') is added a phenol compound of the formula (III') dissolved in a suitable solvent, and a base as a deacidifying agent is reacted at a temperature of from under cooling or from room temperature to the boiling point of the solvent used for 30 min to 24 h to synthesize a phosphonite compound containing phosphinobiphenylene of the formula (I').

The alkyl having 1 to 5 carbon atoms at $R^1$ and $R^2$ in the formula of phenol compound of the formula (III') is exemplified by methyl, ethyl, tert-butyl and the like, preferably tert-butyl. From the aspect of affording a phosphonite compound of the formula (Ia) showing particularly fine stabilizing action, 2,4-di-tert-butylphenol, 2,4-di-tert-butyl-5-methylphenol, 2,4-di-tert-butyl-6-methylphenol and the like (compound of the formula (III)) are preferably used. The solvent in which to dissolve a phenol compound is preferably benzene, chlorobenzene, toluene, xylene, chlorotoluene, hexane, heptane, ethyl ether, tetrahydrofuran, chloroform, carbon tetrachloride, dichloroethane and the like, particularly preferably benzene, toluene and xylene. The base to be suitably used as a deacidifying agent is exemplified by dimethylformamide, triethylamine, tributylamine, morpholine, dimethylaniline, pyridine, picoline, lutidine, collidine, quinoline, isoquinoline, pyrazine, aminopyridine, 1,8-bis(dimethylamino) naphthalene, amine such as 1,8-diazabicyclo[5.4.0]undeca-7-ene and the like, with preference given to pyridine.

The phenol compound is used generally in a 3 to 5-fold molar amount, preferably 3.5 to 4.5-fold molar amount, per mole of biphenyl. The base as a deacidifying agent is used generally in a 0.5 to 2-fold molar amount, preferably 0.8 to 1.5-fold molar amount, per mole of phenol compound. Under cooling means generally not more than 20° C., generally between 5° C. and 15° C.

For synthesis of a phosphonite compound of the formula (I) (when the objective phosphonite compound is synthesized from a phosphine compound of the formula (II) and a phenol compound of the formula (III)), a small amount of a phosphonite compound of the formula (Ib) is produced in addition to a phosphonite compound of the formula (Ia). The effect of the phosphonite compound of the formula (Ib) as a stabilizer of organic polymer materials is fine though somewhat inferior to that of the phosphonite compound of the formula (Ia), and a mixture of these shows superior stabilizing action.

The hydrochloride of a base and a pyridine-aluminum chloride complex contained in the reaction product after production of the objective phosphonite compound can be removed by partitioning, which is performed, for example, as follows. That is, when the mixture is heated to 70–110° C., a pyridine-aluminum chloride complex and hydrochloride of the base become a solution state. This layer and an organic layer (solvent layer) containing the phosphonite compound are separated in two layers, which can be separated by partitioning.

The pyridine-aluminum chloride complex remaining in a solvent layer after the partitioning operation containing the objective phosphonite compound can be certainly removed by treating the solution with alkali or a salt thereof. For example, alkali or a salt thereof is added to a solvent layer containing the objective phosphonite compound in a proportion of 5.1–50 wt %, preferably 10–50 wt %, of the phosphonite compound, which mixture is stirred in a temperature range of 0° C.–50° C. for 30 min –5 h, and the alkali layer and the solvent layer containing the objective phosphonite compound are separated from the solution after stirring, whereby the residual pyridine-aluminum chloride complex is removed. Examples of the alkali and a salt thereof include hydroxide, carbonate, hydrogencarbonate and carboxylate of alkali metal, and oxide, hydroxide, carbonate, hydrogencarbonate and carboxylate of alkaline earth metal. Examples of the alkali metal include lithium, sodium, potassium and rubidium, examples of the hydroxide of alkali metal include lithium hydroxide, sodium hydroxide, potassium hydroxide, rubidium hydroxide and the like, examples of the carbonate of alkali metal include sodium carbonate, potassium carbonate and the like, examples of the hydrogencarbonate of alkali metal include sodium hydrogencarbonate, potassium hydrogencarbonate and the like, and examples of the carboxylate of alkali metal include sodium acetate, potassium acetate and the like. Examples of the alkaline earth metal include magnesium, calcium and barium, examples of the oxide of alkaline earth metal include magnesium oxide, calcium oxide, barium oxide and the like, examples of the hydroxide of alkaline earth metal include magnesium hydroxide, calcium hydroxide and the like, carbonate of alkaline earth metal include magnesium carbonate, calcium carbonate and the like, examples of the hydrogencarbonate of alkaline earth metal include magnesium hydrogencarbonate, calcium hydrogencarbonate and the like, and examples of the carboxylate of alkaline earth metal include magnesium acetate, calcium acetate, barium acetate and the like. The use of hydroxide of alkali metal is preferable, and particularly the use of sodium hydroxide is industrially advantageous. The alkali or a salt thereof is advantageously used particularly as an aqueous solution having a concentration of 20–50 wt % in view of operability.

In this way, a solvent and an unreacted phenol compound are removed from a solvent layer containing a phosphonite compound containing phosphinobiphenylene of the formula (I') but without hydrochloride of a base or a pyridine-aluminum chloride complex, which have been removed, and the objective phosphonite compound can be obtained as a glass-like solid. Generally, the solvent and the unreacted phenol compound are removed by evaporating the solvent and the unreacted phenol compound under reduced pressure.

It is preferable to add hindered amine to a solvent layer after removal of a pyridine-aluminum chloride complex, which contains the objective phosphonite compound, and distill away a solvent and an unreacted phenol compound, thereby to give the objective phosphonite compound.

The hindered amine is preferably a compound having a 2,2,6,6-tetramethyl-4-piperidyl ring or a 1,2,2,6,6-pentamethyl-4-piperidyl ring. Examples of the compound include bis(2,2,6,6-tetramethyl-4-piperidyl)sebacate, bis(1,2,2,6,6-pentamethyl-4-piperidyl)-2-(3,5-di-tert-butyl-4-hydroxybenzyl)-2-n-butylmalonate, bis(1-acryloyl-2,2,6,6-tetramethyl-4-piperidyl) bis(3,5-di-tert-butyl-4-hydroxybenzyl)malonate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, poly{[6-(1,1,3,3-tetramethylbutyl)imino-s-triazine-2,4-diyl][(2,2,6,6-tetramethyl-4-piperidyl)imino]hexamethylene[(2,2,6,6-tetramethyl-4-piperidyl)imino]}, poly{(6-morpholino-s-triazine-2,4-diyl)[(2,2,6,6-tetramethyl-4-piperidyl)imino]hexamethylene[(2,2,6,6-tetramethyl-4-piperidyl)imino]}, 1-hydroxyethyl-2,2,6,6-tetramethyl-4-piperidinol/succinic acid condensate and cyanuric chloride/tert-octylamine/1,6-bis(2,2,6,6-tetramethyl-4-piperidylamino)hexane condensate and the like. Of these, particularly bis(2,2,6,6-tetramethyl-4-piperidyl)sebacate, poly{[6-(1,1,3,3-tetramethylbutyl)imino-s-triazine-2,4-diyl][(2,2,6,6-tetramethyl-4-piperidyl)imino]hexamethylene[(2,2,6,6-tetramethyl-4-piperidyl)imino]} and the like are preferable. The hindered amine is added in such an amount that makes the amount of the hindered amine 0.001–5 wt %, preferably 0.01–1 wt %, relative to the objective phosphonite compound in a glass-like solid.

According to the method of the present invention, the objective phosphonite compound can be ultimately obtained as a highly pure glass-like solid. When, for example, the phosphonite compound of the formula (I) is to be obtained, a highly pure glass-like solid having a content of the phosphonite compound of the formula (I) (content of the compound of the formula (Ia) or content of the compound of the formula (Ia) and the compound of the formula (Ib) in total) of not less than 85%, preferably not less than 90%, can be obtained. The glass-like solid can be separated and purified by a conventional method such as recrystallization, distillation, chromatography and the like.

Best Mode for Embodiment of the Invention

The present invention is explained in detail in the following by referring to Examples, Experimental Examples and Comparative Examples. The present invention is not limited by these examples in any way.

EXAMPLE 1

Biphenyl (30.8 g), aluminum chloride (69.3 g) and phosphorus trichloride (109 g) were charged in a 1 L flask and the mixture was refluxed under heating with stirring at 74–75° C. for 4 h. A hydrogen chloride gas (9.9 g, 67.8% of theoretical value) was generated then. After allowing to cool, pyridine (41.1 g) was added dropwise at 60–70° C., and excess phosphorus trichloride was distilled away from the reaction product at a temperature of 60–80° C. under reduced pressure. Then, 2,4-di-tert-butyl-5-methylphenol (176.4 g) dissolved in toluene (327 g) was added and pyridine (63.3 g) was added dropwise, which was followed by stirring with heating of the mixture at 100° C. for 3 h. This reaction mixture was stood at 80° C. and partitioned between generated hydrochloride of pyridine and a complex of pyridine and aluminum chloride to give a toluene layer (476.8 g). The solvent was distilled away under reduced pressure from this solution to give a yellow glass-like solid (201.2 g, yield 92%, m.p. 96–101° C.) containing tetrakis (2,4-di-tert-butyl-5-methylphenyl)-4,4'-biphenylenediphosphonite as a main component. As a result of the measurement by gel permeation chromatography (Shimadzu LC-5A/TSKgel, hereinafter to be abbreviated as GPC), the purity of tetrakis(2,4-di-tert-butyl-5-methylphenyl)-4,4'-biphenylenediphosphonite was found to be 90%.

Comparative Example 1

Biphenyl (30.8 g), aluminum chloride (69.3 g) and phosphorus trichloride (105 g) were charged in a 1 L flask and the mixture was refluxed under heating with stirring at 74–75° C. for 3.5 h. A hydrogen chloride gas (10.2 g, 68% of theoretical value) was generated then. Excess phosphorus trichloride was distilled away from the reaction product at 55° C. under reduced pressure to give a red-brown oil (146.3 g). Toluene (419 g), 2,4-di-tert-butyl-5-methylphenol (176.7 g) and pyridine (125.7 g) were charged in a 1 L flask and the red-brown oil (146.3 g) was added dropwise over 1 h. The mixture was refluxed under heating at 80° C. for 4 h, and an aluminum chloride layer was separated at 80° C. The upper layer of the toluene layer was cooled to –10° C. and filtrated. The filtrate was concentrated to give a yellow glass-like solid (189.9 g, yield 78%, m.p. 58–65° C.). The purity of tetrakis(2,4-di-tert-butyl-5-methylphenyl)-4,4'-biphenylenediphosphonite as measured by GPC was 66%.

EXAMPLE 2

Biphenyl (92.5 g), aluminum chloride (152 g) and phosphorus trichloride (494.3 g) were charged in a 5 L flask and the mixture was refluxed under heating with stirring at 74–75° C. for 4.5 h. A hydrogen chloride gas (29.1 g, 70.1% of theoretical value) was generated then. After allowing to cool, pyridine (99.2 g) was added dropwise at 60–70° C., and excess phosphorus trichloride was distilled away from the reaction product at a temperature of 60–80° C. under reduced pressure. Then, 2,4-di-tert-butyl-5-methylphenol (475.8 g) dissolved in toluene (982.5 g) was added and pyridine (161.8 g) was added dropwise over about 30 min, which was followed by stirring of the mixture at 100° C. for 3 h. This reaction mixture was stood at 80° C. and partitioned between generated hydrochloride of pyridine and a complex of pyridine and aluminum chloride to give a toluene layer (1431 g). To 358 g of the thus-obtained toluene layer (1431 g) was added 35% aqueous sodium hydroxide (90 g) and the mixture was vigorously stirred at room temperature for 1 h and partitioned to give an alkali layer and a toluene layer. The toluene layer was filtrated. The solvent was distilled away from this solution under reduced pressure to give a yellow glass-like solid (141 g, yield 86%, m.p. 78–82° C.). This yellow glass-like solid was analyzed by GPC. As a result, the solid was a composition containing tetrakis(2,4-di-tert-butyl-5-methylphenyl)-4,4'-biphenylenediphosphonite (content 78%), (2,4-di-tert-butyl-5-methylphenoxy)bis(4'-(bis(2,4-di-tert-butyl-5-methylphenoxy)phosphino)biphenyl-4-yl)phosphine, (2,4-di-tert-butyl-5-methylphenoxy)(4'-(bis(2,4-di-tert-butyl-5-methylphenoxy)phosphino)biphenyl-4-yl)biphenyl-4-yl-phosphine and 4-bis(2,4-di-tert-butyl-5-methylphenoxy)phosphinobiphenyl. The total content of the compound of the formula (I) was 95%.

Comparative Example 2

From the toluene layer (1431 g) obtained in Example 2, 90 g was cooled to –10° C. and filtrated. The solvent was distilled away from this solution under reduced pressure to give a yellow glass-like solid (34.8 g, yield 83%, m.p. 75–80° C.) mainly containing tetrakis(2,4-di-tert-butyl-5-methylphenyl)-4,4'-biphenylene diphosphonite. The yellow glass-like solid was analyzed by GPC. The results were the same as that obtained in Example 2.

Experimental Example 1 (Test for Stability Against Hydrolysis)

The yellow glass-like solids obtained in Example 2 and Comparative Example 2, which contained tetrakis(2,4-di-tert-butyl-5-methylphenyl)-4,4'-biphenylenediphosphonite as a main component, and distilled water were placed in a glass bottle, which was then plugged in and heated to 100° C. The content of tetrakis(2,4-di-tert-butyl-5-methylphenyl)-4,4'-biphenylenediphosphonite at 1 h and 3 h later was measured by GPC, based on which residual percentage was determined. The results are shown in Table 1.

TABLE 1

| | residual rate (%) | | |
| --- | --- | --- | --- |
| | start | 1 h later | 3 h later |
| Sample of Example 2 | 100 | 100 | 100 |
| Sample of Comparative Example 2 | 100 | 95 | 22 |

The initial content of tetrakis(2,4-di-tert-butyl-5-methylphenyl)-4,4'-biphenylene diphosphonite was 100.

As a result, it was found that a treatment with sodium hydroxide gave a phosphonite compound stable with time.

EXAMPLE 3

Biphenyl (30.8 g), aluminum chloride (56.0 g) and phosphorus trichloride (164.8 g) were charged in a 1 L flask and the mixture was refluxed under heating with stirring at 74–75° C. for 10 h. A hydrogen chloride gas (13.0 g, 89% of theoretical value) was generated then. After allowing to cool, pyridine (31.6 g) was added dropwise at 60–70° C., and excess phosphorus trichloride was distilled away from the reaction product at a temperature of 60–80° C. under reduced pressure. Then, 2,4-di-tert-butylphenol (165.1 g) dissolved in toluene (327 g) was added and pyridine (60.1 g) was added dropwise, which was followed by stirring of the mixture at 100° C. for 3 h. This reaction mixture was stood at 80° C. and generated hydrochloride of pyridine and a complex of pyridine and aluminum chloride were separated to give a toluene layer (484 g). Thereto was added 35% aqueous sodium hydroxide (120 g) and the mixture was vigorously stirred at room temperature for 1 h and partitioned to give an alkali layer and a toluene layer, which was followed by filtration. The solvent was distilled away from this solution under reduced pressure to give a yellow glass-like solid (186.6 g, yield 90%, m.p. 95–100° C.). This yellow glass-like solid was analyzed by GPC. As a result, the solid was a composition containing tetrakis(2,4-di-tert-butylphenyl)-4,4'-biphenylenediphosphonite (content 75%), (2,4-di-tert-butylphenoxy)bis(4'-(bis(2,4-di-tert-butylphenoxy)phosphino)biphenyl-4-yl)phosphine, (2,4-di-tert-butylphenoxy)(4'-(bis(2,4-di-tert-butylphenoxy)phosphino)biphenyl-4-yl)biphenyl-4-yl-phosphine and 4-bis(2,4-di-tert-butylphenoxy)phosphinobiphenyl. The total content of the compound of the formula (I) was 95%.

Experimental Example 2

Samples prepared by adding (2,2,6,6-tetramethyl-4-piperidyl)sebacate (also expressed as HALS) to a yellow glass-like solid containing tetrakis(2,4-di-tert-butyl-5-methylphenyl)-4,4'-biphenylenediphosphonite obtained in Example 2 as a main component in a wt % proportion of 0.2%, 0.4% and 0.6% and a sample without the addition were heated to 160° C. in a nitrogen atmosphere. The content of tetrakis(2,4-di-tert-butyl-5-methylphenyl)-4,4'-biphenylenediphosphonite at 3 h and 10 h later was measured by GPC, based on which residual percentage was determined. The results are shown in Table 2.

| Amount of HALS added (%) | residual rate (%) | | |
|---|---|---|---|
| | start | 3 h later | 10 h later |
| 0 | 100 | 96 | 96 |
| 0.2 | 100 | 100 | 98 |
| 0.4 | 100 | 100 | 99 |
| 0.6 | 100 | 100 | 100 |

The initial content of tetrakis(2,4-di-tert-butyl-5-methylphenyl)-4,4'-biphenylene diphosphonite was 100.

The results mentioned above show that the addition of HALS resulted in the inhibition of decomposition at 160° C., confirming the heat stabilization effect.

EXAMPLE 4

Biphenyl (3.86 kg), aluminum chloride (6.30 kg) and phosphorus trichloride (22.65 kg) were charged in a 100 L reaction vessel and the mixture was refluxed under heating with stirring at 74–75° C. for 4 h. A hydrogen chloride gas (1.25 kg, 68.5% of theoretical value) was generated then. After allowing to cool, pyridine (3.94 kg) was added dropwise at 60–70° C., and excess phosphorus trichloride was distilled away from the reaction product at a temperature of 60–80° C. under reduced pressure. Then, 2,4-di-tert-butyl-5-methylphenol (19.85 kg) dissolved in toluene (40.95 kg) was added and pyridine (6.93 kg) was added dropwise, which was followed by stirring with heating of the mixture at 100° C. for 3 h. This reaction mixture was stood at 80° C. and generated hydrochloride of pyridine and a complex of pyridine and aluminum chloride were separated to give a toluene layer (30.9 kg). Thereto was added 35% aqueous sodium hydroxide (15.0 kg) and the mixture was vigorously stirred at room temperature for 2 h and partitioned between an alkali layer and a toluene layer, which was followed by filtration to give a toluene solution (59.11 kg). To this solution was added bis(2,2,6,6-tetramethyl-4-piperidyl)sebacate (50.0 g) and the solvent and unreacted 2,4-di-tert-butyl-5-methylphenol were distilled away under reduced pressure to give a yellow glass-like solid (22 kg, yield 80%, m.p. 104–112° C.) containing tetrakis(2,4-di-tert-butyl-5-methylphenyl)-4,4'-biphenylenediphosphonite as a main component. This yellow glass-like solid was analyzed by GPC. As a result, the solid was a composition containing tetrakis(2,4-di-tert-butyl-5-methylphenyl)-4,4'-biphenylenediphosphonite (content 75%), (2,4-di-tert-butyl-5-methylphenoxy)(4'-(bis(2,4-di-tert-butyl-5-methylphenoxy)phosphino)biphenyl-4-yl)biphenyl-4-yl-phosphine and 4-bis(2,4-di-tert-butyl-5-methylphenoxy)phosphinobiphenyl. The total content of the compound of the formula (I) was 96%.

Experimental Example 3

Biphenyl (92.5 g), aluminum chloride (152 g) and phosphorus trichloride (494.3 g) were charged in a 5 L flask and the mixture was refluxed under heating with stirring at 74–75° C. for 4.5 h. A hydrogen chloride gas (31.1 g, 74.8% of theoretical value) was generated then. After allowing to cool, pyridine (90.2 g) was added dropwise at 60–70° C., and excess phosphorus trichloride was distilled away from the reaction product at a temperature of 60–80° C. under reduced pressure. Then, 2,4-di-tert-butyl-5-methylphenol (475.8 g) dissolved in toluene (982.5 g) was added and pyridine (161.8 g) was added dropwise over about 30 min, which was followed by stirring of the mixture at 100° C. for 3 h. This reaction mixture was stood at 80° C. and generated hydrochloride of pyridine and a complex of pyridine and aluminum chloride were separated to give a toluene layer (1445 g). To the thus-obtained toluene layer (1445 g) was added 35% aqueous sodium hydroxide (360 g) and the mixture was vigorously stirred at room temperature for 1 h and partitioned to give an alkali layer and a toluene layer, which was followed by filtration of the toluene layer to give a toluene solution (1418 g) containing tetrakis(2,4-di-tert-butyl-5-methylphenyl)-4,4'-biphenylenediphosphonite as a main component.

EXAMPLE 5

The toluene solution (355 g) obtained in Experimental Example 3 was charged in a 0.5 L flask and bis(2,2,6,6-tetramethyl-4-piperidyl)sebacate (0.33 g) was added. The residual toluene was distilled away under reduced pressure in a nitrogen atmosphere at a temperature of 40–130° C. The residual toluene and unreacted 2,4-di-tert-butyl-5-methylphenol were distilled away under reduced pressure in a nitrogen atmosphere at a temperature of 160–170° C. The content of tetrakis(2,4-di-tert-butyl-5-methylphenyl)-4,4'-biphenylenediphosphonite and 2,4-di-tert-butyl-5-methylphenol at 1 h, 3 h and 5 h from the start of concentration was measured by GPC.

Comparative Example 3

The toluene solution (355 g) obtained in Experimental Example 3 was charged in a 0.5 L flask and the residual toluene was distilled away under reduced pressure in a nitrogen atmosphere at a temperature of 40–130° C. The residual toluene and unreacted 2,4-di-tert-butyl-5-methylphenol were distilled away under reduced pressure in a nitrogen atmosphere at a temperature of 160–170° C. The content of tetrakis(2,4-di-tert-butyl-5-methylphenyl)-4,4'-biphenylenediphosphonite and 2,4-di-tert-butyl-5-methylphenol at 1 h, 3 h and 5 h from the start of concentration was measured by GPC.

The results of the above-mentioned Example 5 and Comparative Example 3 are shown in the following Table 3.

TABLE 3

|  | 1 h | 3 h | 5 h |
|---|---|---|---|
| Example 5 | A: 72.5% | A: 74.6% | A: 74.8% |
|  | B: 3.5% | B: 0.4% | B: 0.3% |
| Comparative | A: 72.7% | A: 73.5% | A: 72.9% |
| Example 3 | B: 3.8% | B: 1.3% | B: 1.9% |

A: tetrakis(2,4-di-tert-butyl-5-methylphenyl)-4,4'-biphenylenediphosphonite

B: 2,4-tert-butyl-5-methylphenol

From Table 3, it is clear that addition of bis(2,2,6,6-tetramethyl-4-piperidyl)sebacate resulted in the suppression of the thermal decomposition of tetrakis(2,4-di-tert-butyl-5-methylphenyl)-4,4'-biphenylenediphosphonite during concentration and sufficient reduction of the residual 2,4-di-tert-butyl-5-methylphenol.

INDUSTRIAL APPLICABILITY

According to the present invention, a high quality phosphonite compound containing phosphinobiphenylene of the aforementioned formula (I') can be produced safely in a high yield. In addition, thermal decomposition of the phosphonite compound when heating a solution containing the phosphonite compound can be prevented.

This application is based on a patent application No. 1505/1999 filed in Japan, the contents of which are hereby incorporated by reference.

What is claimed is:

1. A method for producing a phosphonite compound comprising phosphinobiphenylene of the formula:

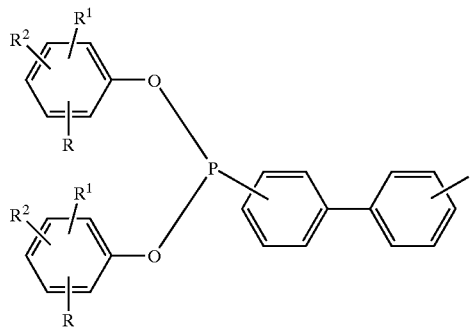

wherein R is a hydrogen atom or methyl and $R^1$ and $R^2$ are each a hydrogen atom or alkyl having 1 to 5 carbon atoms, which method comprising reacting biphenyl and phosphorus trichloride in the presence of aluminum chloride, removing a hydrogen chloride gas generated, adding a pyridine, removing excess phosphorus trichloride, reacting a resulting reaction product containing a phosphine compound of the formula:

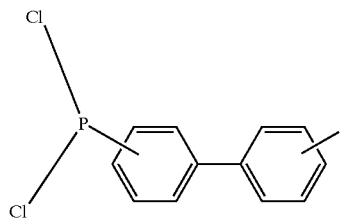

and a phenol compound of the formula:

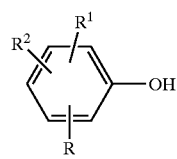

wherein R is a hydrogen atom or methyl and $R^1$ and $R^2$ are each a hydrogen atom or alkyl having 1 to 5 carbon atoms, in the presence of a base as a deacidifying agent, and removing hydrochloride of said base and a pyridine-aluminum chloride complex.

2. A method for producing at least one phosphonite compound of the formula:

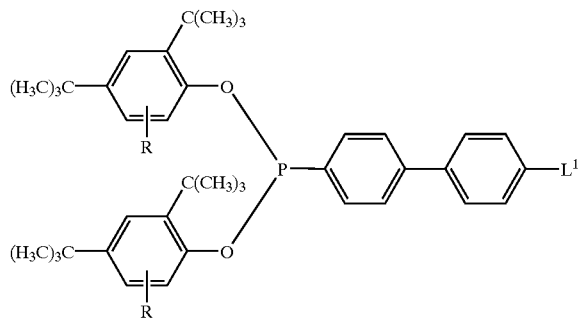

wherein R is a hydrogen atom or methyl and L¹ is a hydrogen atom, a group of the formula:

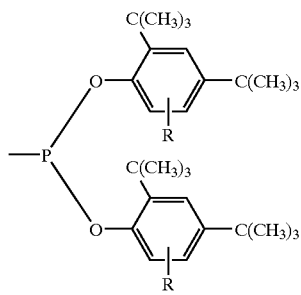

wherein R is as defined above, a group of the formula:

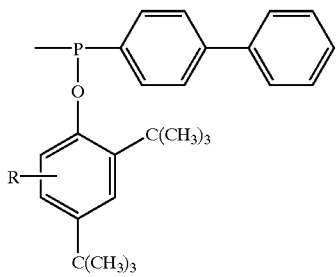

wherein R is as defined above, or a group of the formula:

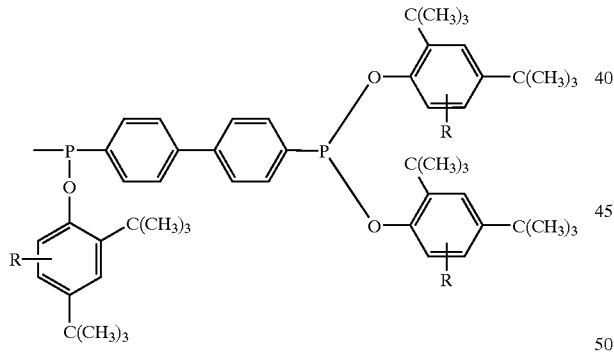

wherein R is as defined above, which method comprising reacting biphenyl and phosphorus trichloride in the presence of aluminum chloride,
removing a hydrogen chloride gas generated,
adding a pyridine,
removing excess phosphorus trichloride,
reacting a resulting reaction product containing at least one phosphine compound of the formula:

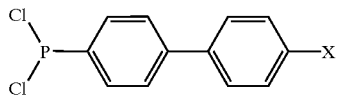

wherein X is a hydrogen atom, —PCl$_2$,

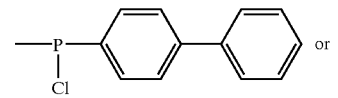

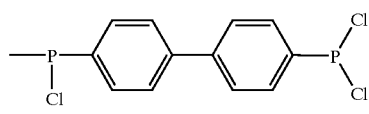

and a phenol compound of the formula:

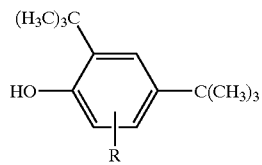

wherein R is a hydrogen atom or methyl, in the presence of a base as a deacidifying agent, and removing hydrochloride of said base and a pyridine-aluminum chloride complex.

3. The method according to claim 2, wherein the phosphonite compound comprises a compound of the formula:

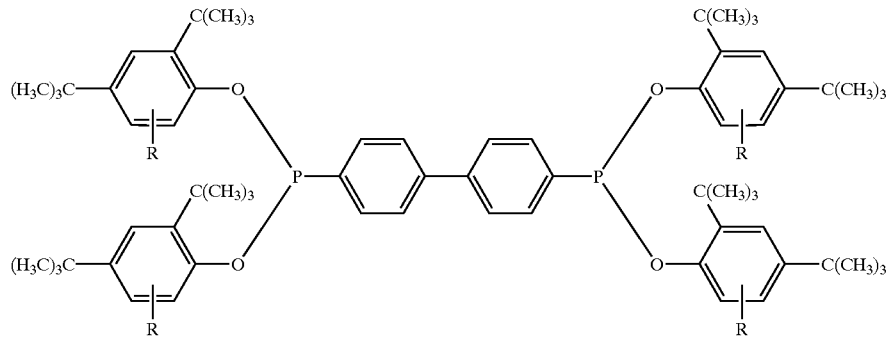

wherein R is a hydrogen atom or methyl, and may further comprise at least one compound selected from compounds of the formula:

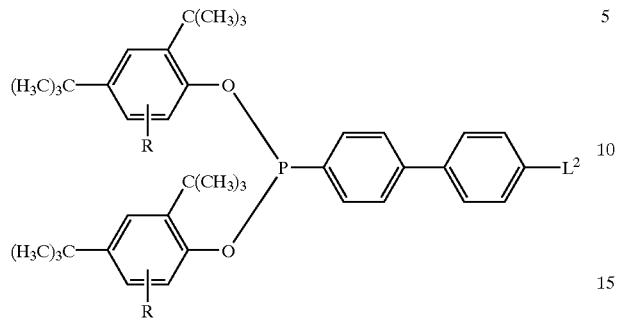

wherein R is a hydrogen atom or methyl and $L^2$ is a hydrogen atom, a group of the formula:

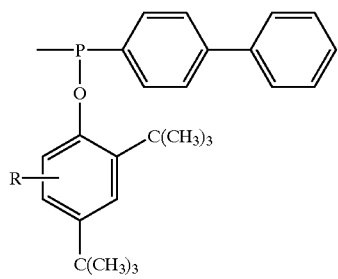

wherein R is as defined above, and a group of the formula:

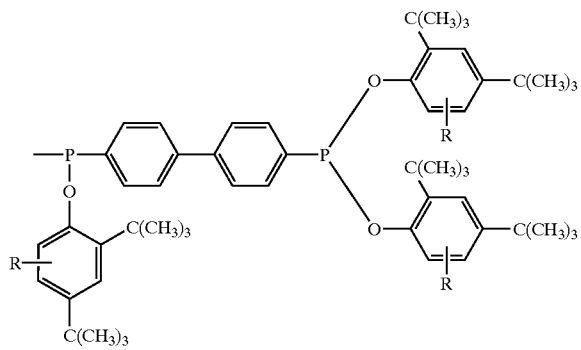

wherein R is as defined above.

4. A method for producing a phosphonite compound comprising phosphinobiphenylene of the formula:

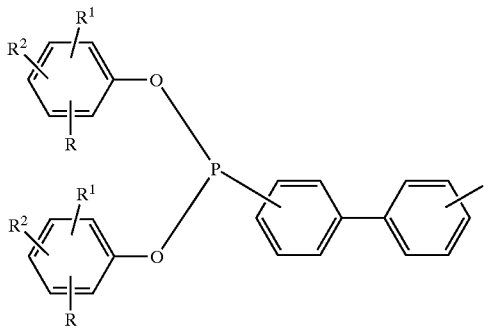

wherein R is a hydrogen atom or methyl and $R^1$ and $R^2$ are each a hydrogen atom or alkyl having 1 to 5 carbon atoms, which method comprising reacting biphenyl and phosphorus trichloride in the presence of aluminum chloride, removing a hydrogen chloride gas generated, adding a pyridine, removing excess phosphorus trichloride, reacting a resulting reaction product containing a phosphine compound of the formula:

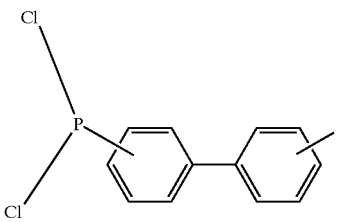

and a phenol compound of the formula:

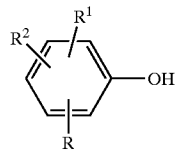

wherein R is a hydrogen atom or methyl and $R^1$ and $R^2$ are each a hydrogen atom or alkyl having 1 to 5 carbon atoms, in the presence of a base as a deacidifying agent, removing hydrochloride of said base and a pyridine-aluminum chloride complex, and treating an obtained crude product with alkali or a salt thereof.

5. A method for producing at least one phosphonite compound of the formula:

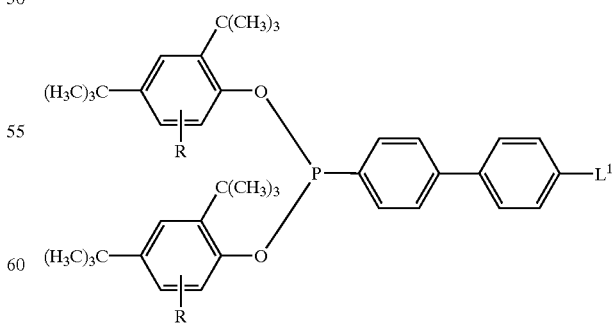

wherein R is a hydrogen atom or methyl and $L^1$ is a hydrogen atom, a group of the formula:

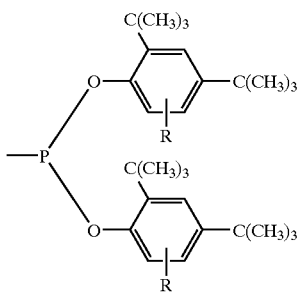

wherein R is as defined above, a group of the formula:

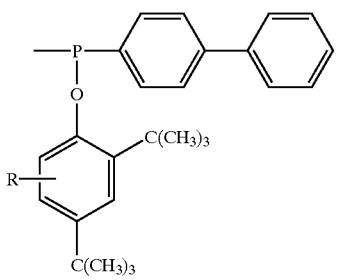

wherein R is as defined above, or a group of the formula:

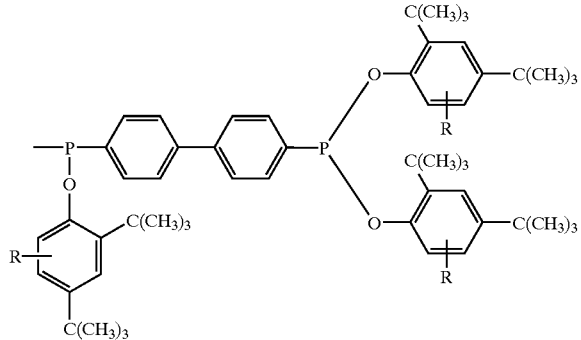

wherein R is as defined above, which method comprising
reacting biphenyl and phosphorus trichloride in the presence of aluminum chloride,
removing a hydrogen chloride gas generated,
adding a pyridine,
removing excess phosphorus trichloride,
reacting a resulting reaction product containing at least one phosphine compound of the formula:

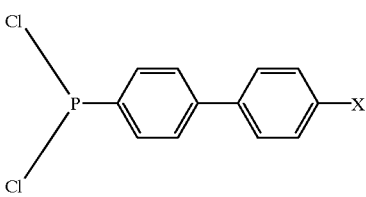

wherein X is a hydrogen atom, —PCl$_2$,

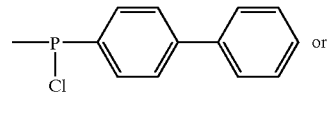

or

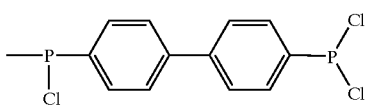

and a phenol compound of the formula:

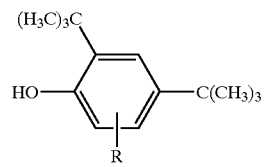

wherein R is a hydrogen atom or methyl, in the presence of a base as a deacidifying agent,
removing hydrochloride of said base and a pyridine-aluminum chloride complex, and
treating an obtained crude product with alkali or a salt thereof.

6. The method according to claim 5, wherein the phosphonite compound comprises a compound of the formula:

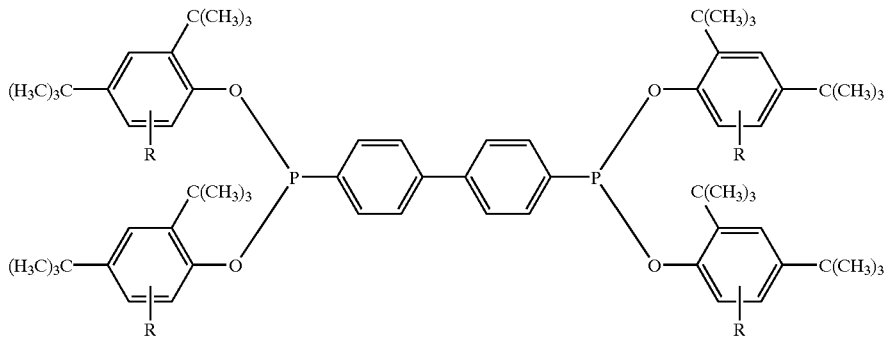

wherein R is a hydrogen atom or methyl, and may further comprise at least one compound selected from compounds of the formula:

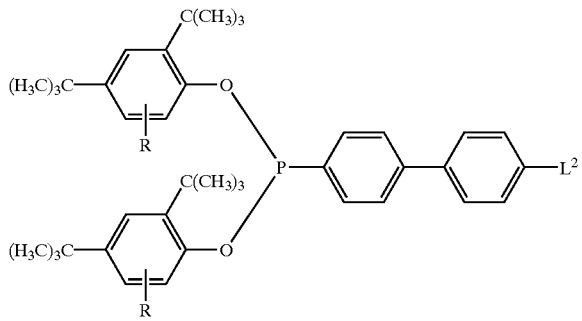

wherein R is a hydrogen atom or methyl and $L^2$ is a hydrogen atom, a group of the formula:

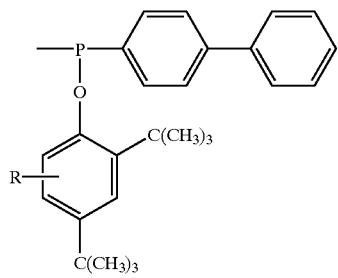

wherein R is as defined above, and a group of the formula:

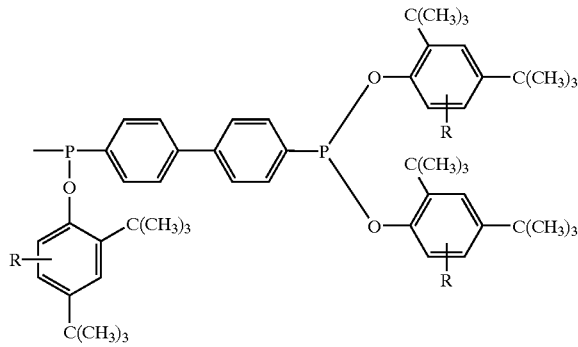

wherein R is as defined above.

7. A method for producing a phosphonite compound comprising phosphinobiphenylene of the formula:

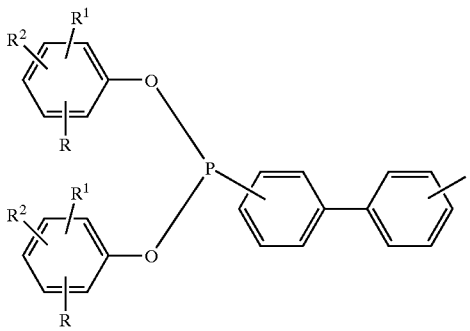

wherein R is a hydrogen atom or methyl and $R^1$ and $R^2$ are each a hydrogen atom or alkyl having 1 to 5 carbon atoms, which method comprising reacting biphenyl and phosphorus trichloride in the presence of aluminum chloride, removing a hydrogen chloride gas generated, adding a pyridine, removing excess phosphorus trichloride, reacting a resulting reaction product containing a phosphine compound of the formula:

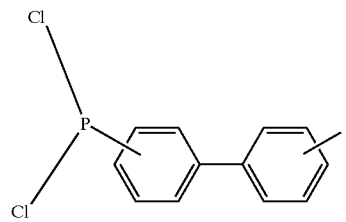

and a phenol compound of the formula:

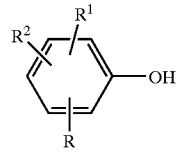

wherein R is a hydrogen atom or methyl and $R^1$ and $R^2$ are each a hydrogen atom or alkyl having 1 to 5 carbon atoms, in the presence of a base as a deacidifying agent, removing hydrochloride of said base and a pyridine-aluminum chloride complex, treating an obtained crude product with alkali or a salt thereof, and removing an unreacted phenol compound.

8. A method for producing at least one phosphonite compound of the formula:

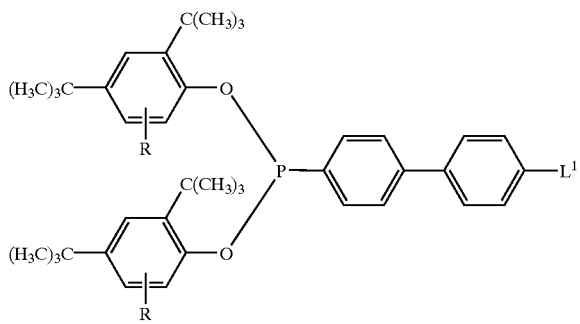

wherein R is a hydrogen atom or methyl and L¹ is a hydrogen atom, a group of the formula:

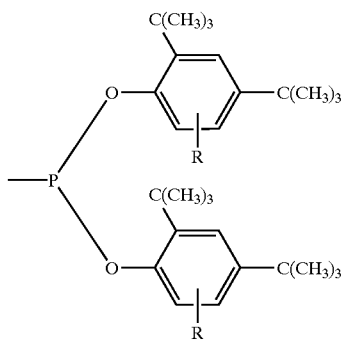

wherein R is as defined above, a group of the formula:

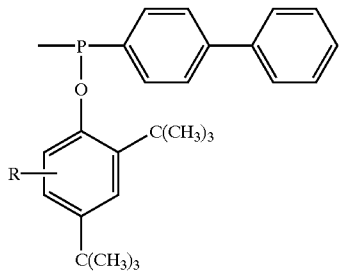

wherein R is as defined above, or a group of the formula:

wherein R is as defined above, which method comprising reacting biphenyl and phosphorus trichloride in the presence of aluminum chloride, removing a hydrogen chloride gas generated, adding a pyridine, removing excess phosphorus trichloride, reacting a resulting reaction product containing at least one phosphine compound of the formula:

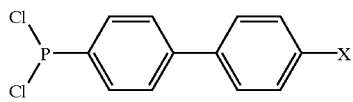

wherein X is a hydrogen atom, —PCl₂,

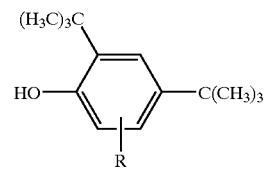 or

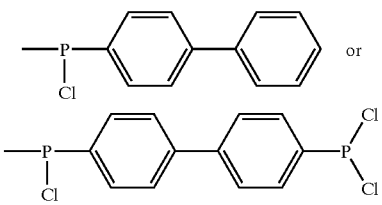

and a phenol compound of the formula:

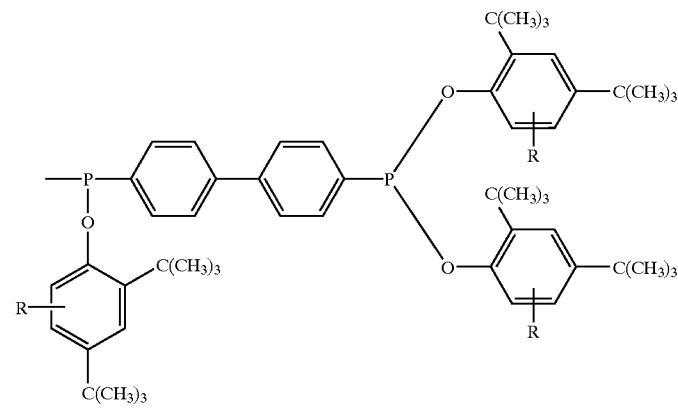

wherein R is a hydrogen atom or methyl, in the presence of a base as a deacidifying agent, removing hydrochloride of said base and a pyridine-aluminum chloride complex, treating an obtained crude product with alkali or a salt thereof, and removing an unreacted phenol compound.

9. The method according to claim 8, wherein the phosphonite compound comprises a compound of the formula:

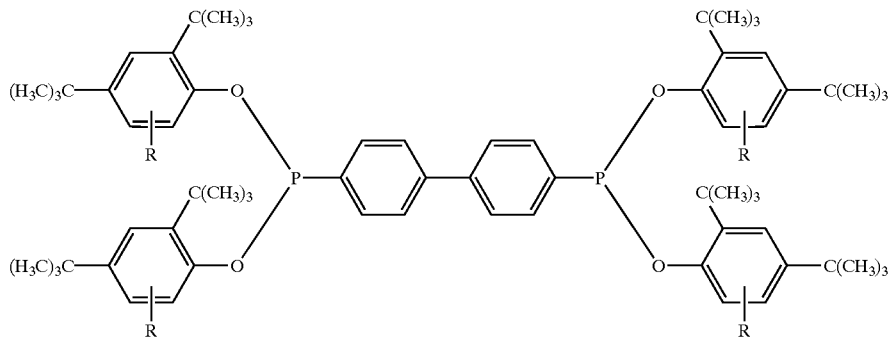

wherein R is a hydrogen atom or methyl, and may further comprise at least one compound selected from compounds of the formula:

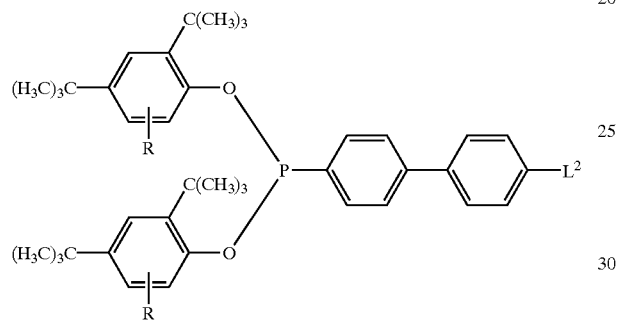

wherein R is a hydrogen atom or methyl and $L^2$ is a hydrogen atom, a group of the formula:

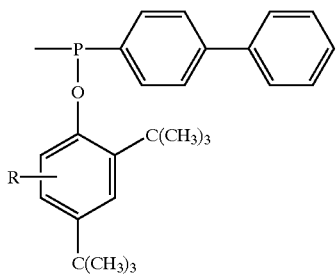

wherein R is as defined above, and a group of the formula:

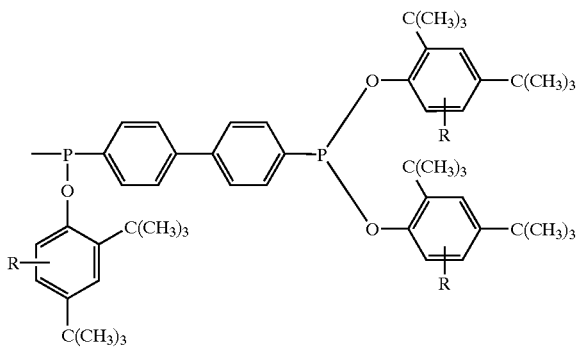

wherein R is as defined above.

10. A method for producing a phosphonite compound comprising phosphinobiphenylene of the formula:

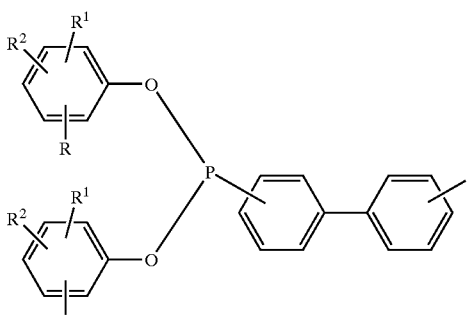

wherein R is a hydrogen atom or methyl and $R^1$ and $R^2$ are each a hydrogen atom or alkyl having 1 to 5 carbon atoms, which method comprising
  reacting biphenyl and phosphorus trichloride in the presence of aluminum chloride,
  removing a hydrogen chloride gas generated,
  adding a pyridine,
  removing excess phosphorus trichloride,
  reacting a resulting reaction product containing a phosphine compound of the formula:

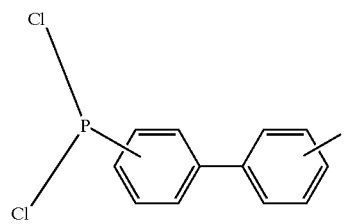

and a phenol compound of the formula:

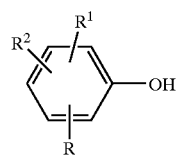

wherein R is a hydrogen atom or methyl and $R^1$ and $R^2$ are each a hydrogen atom or alkyl having 1 to 5 carbon atoms, in the presence of a base as a deacidifying agent,
  removing hydrochloride of said base and a pyridine-aluminum chloride complex, and
  treating an obtained crude product with alkali or a salt thereof, and then with hindered amine.

11. A method for producing at least one phosphonite compound of the formula:

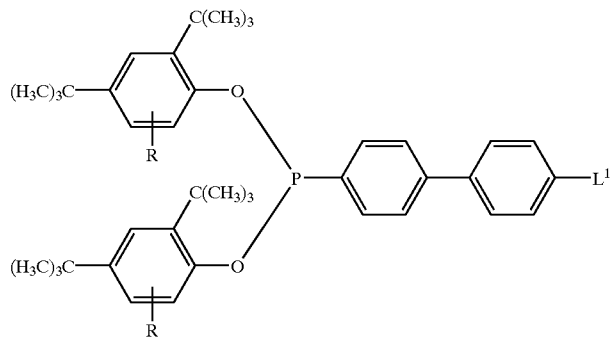

wherein R is a hydrogen atom or methyl and $L^1$ is a hydrogen atom, a group of the formula:

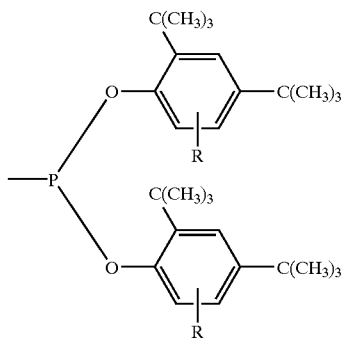

wherein R is as defined above, a group of the formula:

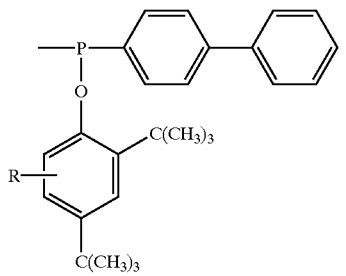

wherein R is as defined above, or a group of the formula:

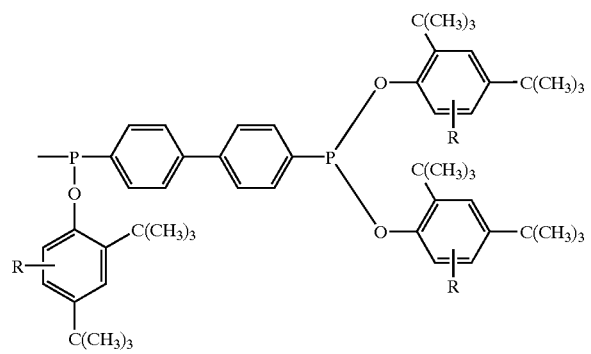

wherein R is as defined above, which method comprising
reacting biphenyl and phosphorus trichloride in the presence of aluminum chloride,
removing a hydrogen chloride gas generated,
adding a pyridine,
removing excess phosphorus trichloride,
reacting a resulting reaction product containing at least one phosphine compound of the formula:

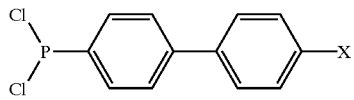

wherein X is a hydrogen atom, $-PCl_2$,

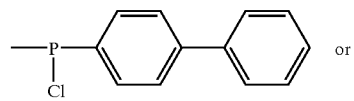

or

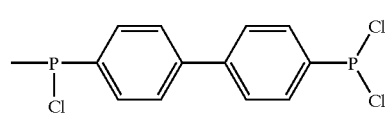

and a phenol compound of the formula:

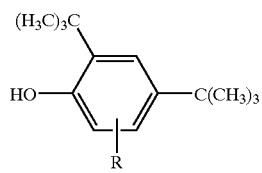

wherein R is a hydrogen atom or methyl, in the presence of a base as a deacidifying agent, and removing hydrochloride of said base and a pyridine-aluminum chloride complex, and treating an obtained crude product with alkali or a salt thereof, and then with hindered amine.

12. The method according to claim 11, wherein the phosphonite compound comprises a compound of the formula:

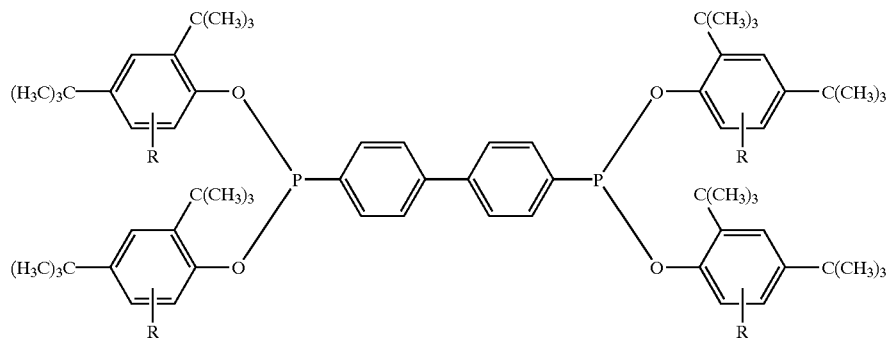

wherein R is a hydrogen atom or methyl, and may further comprise at least one compound selected from compounds of the formula:

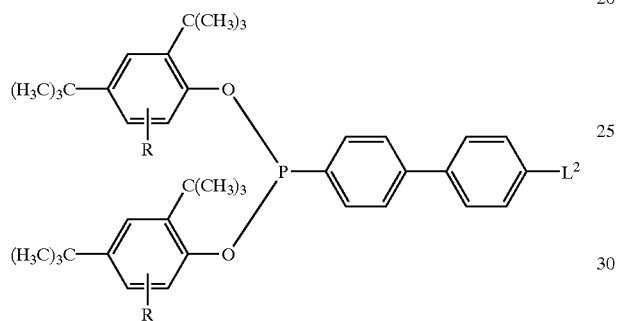

wherein R is a hydrogen atom or methyl and $L^2$ is a hydrogen atom, a group of the formula:

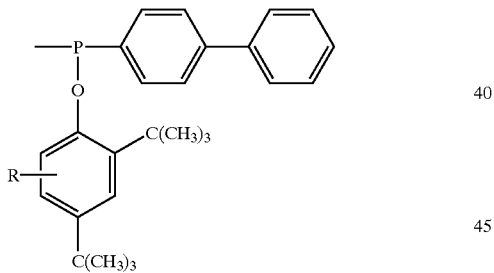

wherein R is as defined above, and a group of the formula:

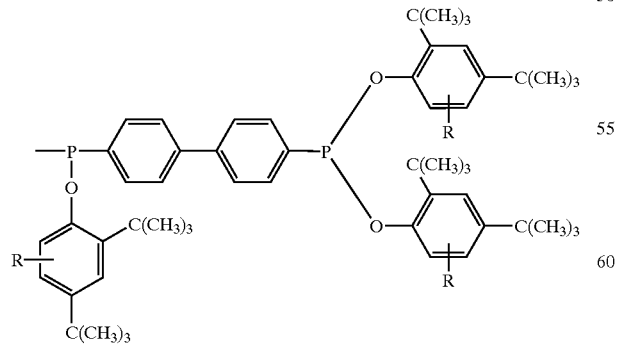

wherein R is as defined above.

13. A method for producing a phosphonite compound comprising phosphinobiphenylene of the formula:

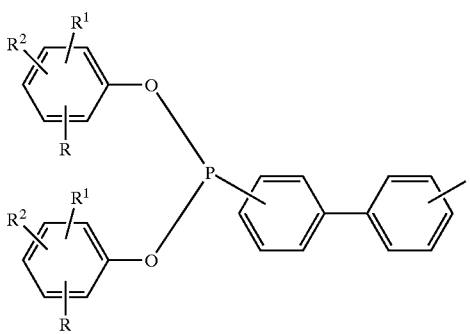

wherein R is a hydrogen atom or methyl and $R^1$ and $R^2$ are each a hydrogen atom or alkyl having 1 to 5 carbon atoms, which method comprising reacting biphenyl and phosphorus trichloride in the presence of aluminum chloride, removing a hydrogen chloride gas generated, adding a pyridine, removing excess phosphorus trichloride, reacting a resulting reaction product containing a phosphine compound of the formula:

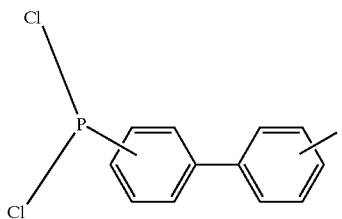

and a phenol compound of the formula:

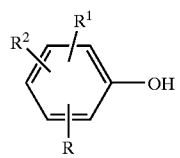

wherein R is a hydrogen atom or methyl and $R^1$ and $R^2$ are each a hydrogen atom or alkyl having 1 to 5 carbon atoms, in the presence of a base as a deacidifying agent, removing hydrochloride of said base and a pyridine-aluminum chloride complex, treating an obtained crude product with alkali or a salt thereof, and then with hindered amine, and removing an unreacted phenol compound.

14. A method for producing at least one phosphonite compound of the formula:

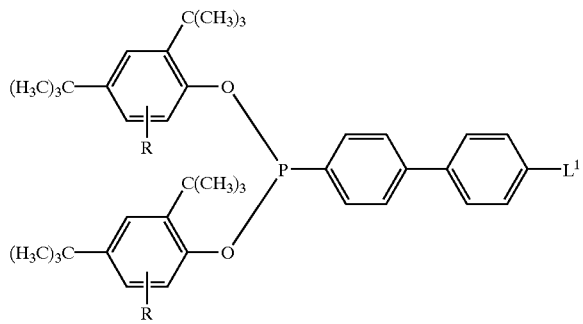

wherein R is a hydrogen atom or methyl and $L^1$ is a hydrogen atom, a group of the formula:

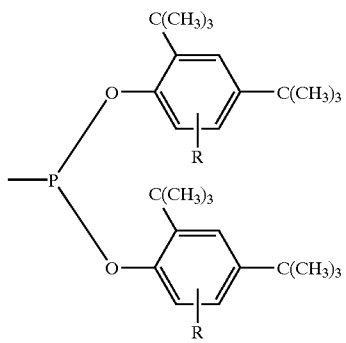

wherein R is as defined above, a group of the formula:

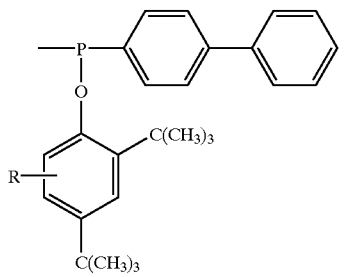

wherein R is as defined above, or a group of the formula:

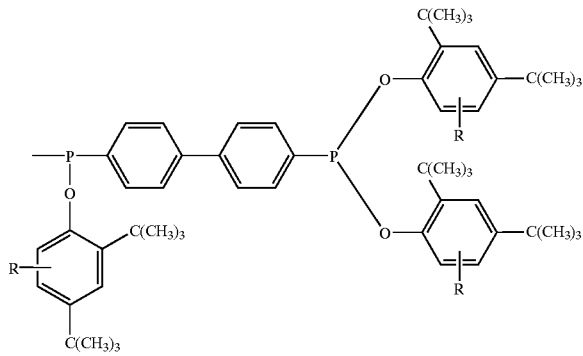

wherein R is as defined above, which method comprising reacting biphenyl and phosphorus trichloride in the presence of aluminum chloride, removing a hydrogen chloride gas generated, adding a pyridine, removing excess phosphorus trichloride, reacting a resulting reaction product containing at least one phosphine compound of the formula:

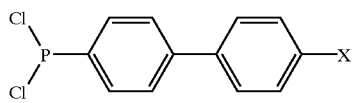

wherein X is a hydrogen atom, $-PCl_2$,

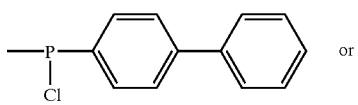 or

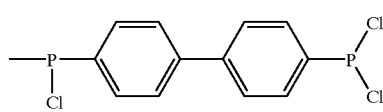

and a phenol compound of the formula:

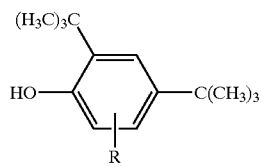

wherein R is a hydrogen atom or methyl, in the presence of a base as a deacidifying agent, removing hydrochloride of said base and a pyridine-aluminum chloride complex, treating an obtained crude product with alkali or a salt thereof and then with hindered amine, and removing an unreacted phenol compound.

15. The method according to claim 14, wherein the phosphonite compound comprises a compound of the formula:

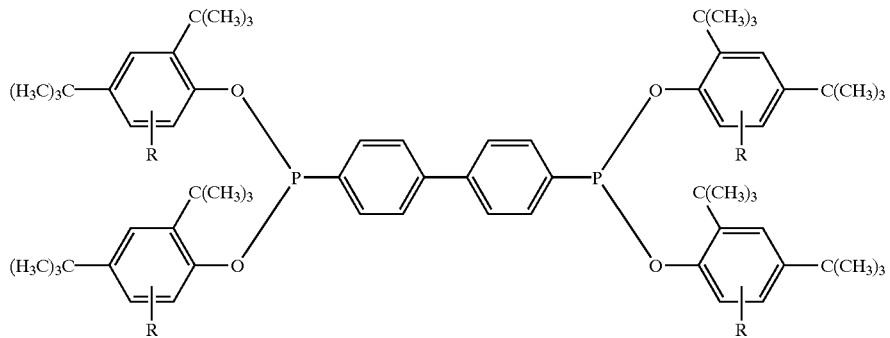

wherein R is a hydrogen atom or methyl, and may further comprise at least one compound selected from compounds of the formula:

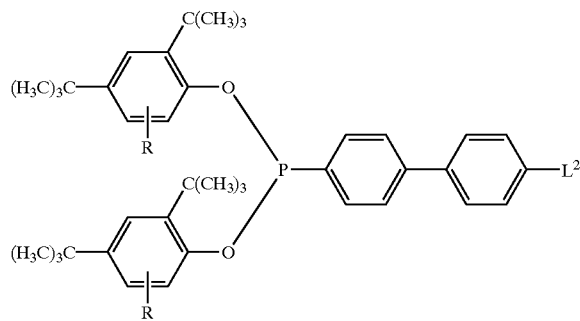

wherein R is a hydrogen atom or methyl and $L^2$ is a hydrogen atom, a group of the formula:

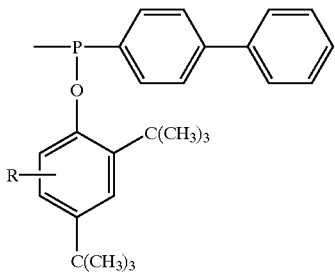

wherein R is as defined above, and a group of the formula:

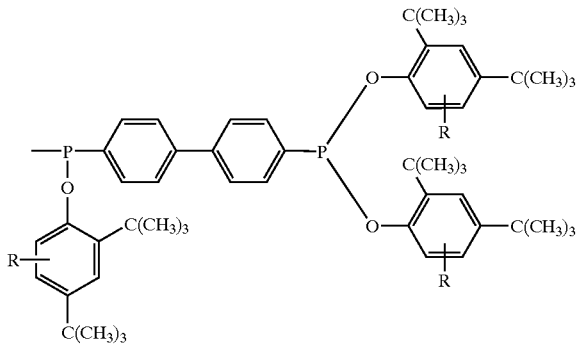

wherein R is as defined above.

16. The method of any one of claims 1, 2, 3, 4, 5, 6, 7, 8, 9, 10, 11, 12, 13, 14 and 15, wherein the pyridine is pyridine, picoline, lutidine, collidine, quinoline, isoquinoline, pyrazine, aminopyridine, pyridazine, pyrimidine, cinnoline or pteridine.

17. The method of any one of claims 1, 2, 3, 4, 5, 6, 7, 8, 9, 10, 11, 12, 13, 14 and 15, wherein the base as a deacidifying agent is selected from dimethylformamide, triethylamine, tributylamine, morpholine, dimethylaniline, pyridine, picoline, lutidine, collidine, quinoline, isoquinoline, pyrazine, aminopyridine, 1,8-bis (dimethylamino)naphthalene and 1,8-diazabicyclo[5.4.0] undeca-7-ene.

18. The method of any one of claims 4, 5, 6, 7, 8, 9, 10, 11, 12, 13, 14 and 15, wherein the alkali or a salt thereof is a hydroxide, carbonate, hydrogencarbonate or carboxylate of an alkali metal or an oxide, hydroxide, carbonate, hydrogencarbonate or carboxylate of an alkaline earth metal.

19. The method of any one of claims 4, 5, 6, 7, 8, 9, 10, 11, 12, 13, 14 and 15, wherein the alkali or a salt thereof is an alkali metal hydroxide.

20. The method of claim 19, wherein the alkali metal hydroxide is sodium hydroxide or potassium hyroxide.

21. The method of any one of claims 4, 5, 6, 7, 8, 9, 10, 11, 12, 13, 14 and 15, wherein the alkali or a salt thereof is used as a 10–50 wt % aqueous solution.

22. The method of any one of claims 10, 11, 12, 13, 14 and 15, wherein the hindered amine is a compound having a 2,2,6,6-tetramethyl-4-piperidyl ring or a 1,2,2,6,6-pentamethyl-4-piperidyl ring.

23. The method of claim 22, wherein the compound having a 2,2,6,6-tetramethyl-4-piperidyl ring or a 1,2,2,6,6-pentamethyl-4-piperidyl ring is a compound selected from bis(2,2,6,6-tetramethyl-4-piperidyl)sebacate, bis(1,2,2,6,6-pentamethyl-4-piperidyl)-2-(3,5-di-tert-butyl-4-hydroxybenzyl)-2-n-butylmalonate, bis(1-acryloyl-2,2,6,6-tetramethyl-4-piperidyl)bis(3,5-di-tert-butyl-4-hydroxybenzyl)malonate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, poly{[6-(1,1,3,3-tetramethylbutyl)imino-s-triazine-2,4-diyl] [(2,2,6,6-tetramethyl-4-piperidyl)imino]hexamethylene[(2,2,6,6-tetramethyl-4-piperidyl)imino]}, poly{(6-morpholino-s-triazine-2,4-diyl)[(2,2,6,6-tetramethyl-4-piperidyl)imino]hexamethylene[(2,2,6,6-tetramethyl-4-piperidyl)imino]}, 1-hydroxyethyl-2,2,6,6-tetramethyl-4-piperidinol/succinic acid condensate and cyanuric chloride/tert-octylamine/1,6-bis(2,2,6,6-tetramethyl-4-piperidylamino)hexane condensate.

24. A method for preventing thermal decomposition of a phosphonite compound, which method comprises heating a solution comprising the phosphonite compound having phosphinobiphenylene of the formula:

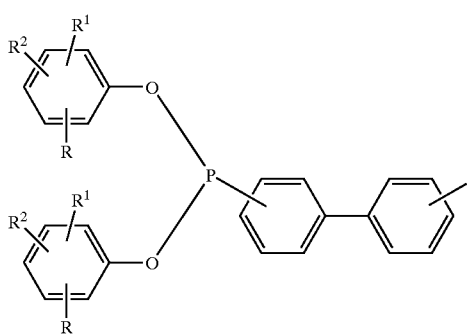

wherein R is a hydrogen atom or methyl and $R^1$ and $R^2$ are each a hydrogen atom or alkyl having 1 to 5 carbon atoms, and a hindered amine, at not less than 150° C. in the presence of hindered amine.

25. A method for preventing thermal decomposition of a phosphonite compound, which method comprises heating, at not less than 150° C. in the presence of hindered amine, a solution comprising at least one phosphonite compound of the formula:

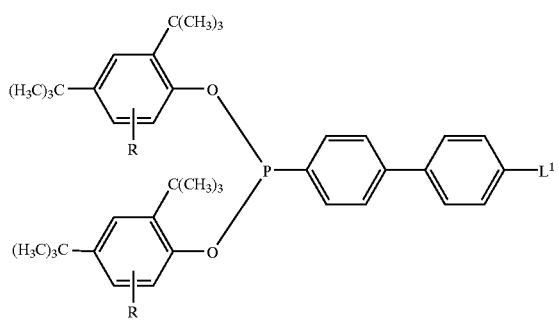

wherein R is a hydrogen atom or methyl and $L^1$ is a hydrogen atom, a group of the formula:

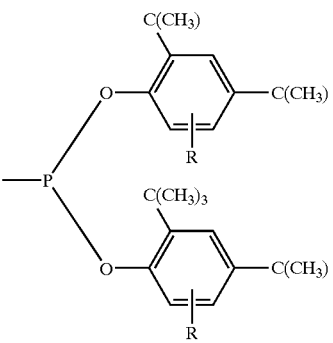

wherein R is as defined above, a group of the formula:

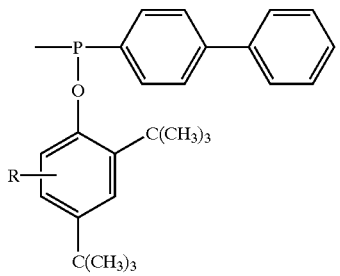

wherein R is as defined above, or a group of the formula:

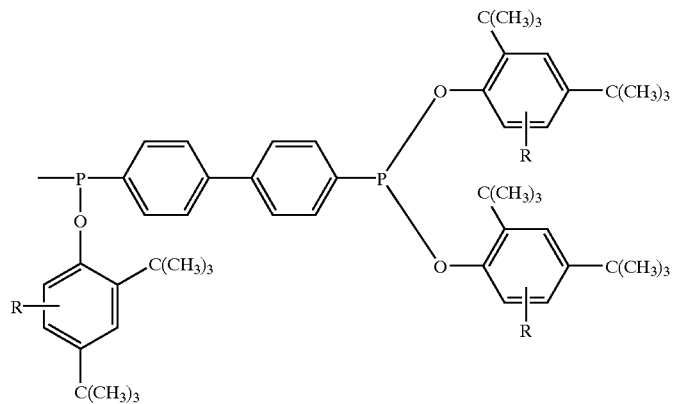

wherein R is as defined above.

* * * * *